(12) United States Patent
Wiedenhoefer

(10) Patent No.: US 6,786,405 B2
(45) Date of Patent: Sep. 7, 2004

(54) TISSUE AND IMPLANT PRODUCT SUPPLY SYSTEM AND METHOD

(76) Inventor: Curt Wiedenhoefer, 502 Waxwing Pl., Davis, CA (US) 95616

( * ) Notice: Subject to any disclaimer, the term of this patent is extended or adjusted under 35 U.S.C. 154(b) by 0 days.

(21) Appl. No.: 10/084,483

(22) Filed: Feb. 28, 2002

(65) Prior Publication Data

US 2003/0160101 A1 Aug. 28, 2003

(51) Int. Cl.[7] .............................................. G06K 15/00
(52) U.S. Cl. ............. 235/385; 235/462.46; 235/472.01; 235/472.03
(58) Field of Search ........................... 235/385, 462.46, 235/472.01, 472.02, 375, 380, 462.45; 705/2, 3, 28

(56) References Cited

U.S. PATENT DOCUMENTS

| 5,832,422 | A | | 11/1998 | Wiedenhoefer | |
|---|---|---|---|---|---|
| 5,986,568 | A | * | 11/1999 | Suzuki et al. | 340/825.52 |
| 6,117,073 | A | * | 9/2000 | Jones et al. | 600/300 |
| 6,283,761 | B1 | * | 9/2001 | Joao | 434/236 |
| 6,375,077 | B1 | * | 4/2002 | Hankins | 235/462.45 |
| 6,385,593 | B2 | * | 5/2002 | Linberg | 705/28 |
| 6,418,346 | B1 | * | 7/2002 | Nelson et al. | 607/59 |
| 6,424,332 | B1 | * | 7/2002 | Powell | 345/156 |
| 6,470,234 | B1 | * | 10/2002 | McGrady | 700/241 |
| 6,493,724 | B1 | * | 12/2002 | Cusack et al. | 707/104.1 |

* cited by examiner

Primary Examiner—Michael G. Lee
Assistant Examiner—Ahshik Kim
(74) Attorney, Agent, or Firm—Stevens, Davis, Miller & Mosher, L.L.P.

(57) ABSTRACT

An electronic hand held wireless device and system are provided to implement various inventorying and/or ordering of implant and/or tissue products from remote sites. The invention also provides a method whereby the hand held device, when in communication with a data base remote from said wireless device, permits real time inventory of available products to be ascertained and real time wireless remote ordering of such products can be effected. Other information, such as product specification, storage requirements and surgical techniques can also be accessed by the hand held device.

4 Claims, 3 Drawing Sheets

TISSUE AND IMPLANT PRODUCT SUPPLY SYSTEM AND METHOD

FIELD OF THE INVENTION

This invention relates to a supply system and method of harvesting, inventorying, selecting and delivering tissue and implant products, with optional governmental, reporting and associated hardware including a mobile hand held electronic user device that synchronizes with a base system including features which provide feedback to the base system regarding the supplied product.

BACKGROUND OF THE INVENTION

Medical procedures involving implantation of replacement tissue and devices have unique product supply requirements. For live tissue, there are supply issues including locating donors and keeping donated tissue alive, delivering and inventorying live tissue, as well as determining criteria for use of the tissue in a living patient. For this and other types of implants and tissue, there are further issues concerning size, shape, availability, surgical techniques, and, after implantation, monitoring. Finally, there are sales, accounting, and government regulatory reporting requirements. While many systems exist which address these issues, none provide an integrated solution which supports the user in the field, typically a sales/marketing representative or a representative of a provider of implant/tissue services.

SUMMARY OF THE INVENTION

The present invention provides a tissue and implant product acquisition and supply system which supports users in the field with a wireless phone line modem web served or free standing mobile hand-held device (hereinafter for ease of description as "wireless hand held electronic device") that synchronizes with a base system, such as a personal computer, private/public network based system, Web-server, etc.

FIG. 1 illustrates one embodiment of a typical tissue and implant supplier's interface for a wireless hand held electronic device, e.g., a hand held personal digital assistant. It is to be understood that such a devices provides typical user options such as e-mail, voice messaging, personal lists, etc. This embodiment provides not only a conduit for channeling user requests to a supplier and responses from the supplier but also provides an extensible support infrastructure by capturing requirements, assisting in harvesting and tracking, including, for example, height/weight and body mass, deformations or abnormalities of the donor, placing orders, managing catalogs and inventory, in addition to delivering messages and providing e-mail and facsimile, etc., in the hand held's databases; and synchronizing with databases of suppliers' base systems. The availability of products, feedback on storage and use of products, and other essential information is kept up-to-date, including confirmation of orders placed and is always accessible by end-users in the supply system of the present invention.

Because of the unique procedural and specification requirements of tissue products and implants, the wireless device can be used to provide camera images of a target site to a supplier before, during and after surgery. The camera can, thus, be used to document the condition of tissue or implant immediately before and/or during or after surgery. Further, a Measuring System (such as the device of U.S. Pat. No. 5,832,422 to Wiedenhoefer the entire specification of which is hereby incorporated by reference as if explicitly set forth herein) can provide a set of precise measurements of the target to facilitate the selection of a tissue product or implant. Finally, a supplier can provide video output to the hand-held, e.g., to educate a surgeon in the use of a new device or to provide x-rays or CT/MRI scans, including a measurement marker on the x-ray or a reference scale on the CT/MRI scan so that the user can determine at least one of a size of the implant or tissue or any object in the image of any segment thereof or angle on the image. The foregoing are meant as exemplary embodiments only and not in any limiting sense.

Once a tissue product or device has been implanted, the product is assigned to a patient record and the patient receiving the product can be monitored and base system inventory can be adjusted by updating the databases resident on the supplier's base station during a synchronization operation.

In such an embodiment, data regarding transactions involving products provided by suppliers is captured in databases stored in the wireless mobile hand-held device and these hand-held databases are synchronized with corresponding supplier databases stored on Web-servers, personal computers, etc., of supplier systems.

The present invention is thus a resource tool for medical provider users and supplier sales/marketing representatives alike. Using the present invention, up-to-date product information is instantly accessible through wireless communications or Phone Line modem, even to a surgeon performing surgery in an operating room. Additional advantages are the automation of the documentation and accounting processes between medical suppliers and medical facilities. Such advantages include, for example, an automated accounting process which results in a reduction of data input errors and unrecorded inventory movement. The invention can assist in providing expedited patient diagnosis, up to date product information and automated governmental reporting. It may also be used to show to potential donor families a high standard for care for the movement of donated tissues and may result in improvements in acquisition and distribution of precious donor tissue resulting in increased amounts of donor to patient activity. Appendix I is a table summarizing the supporting features of the present invention and the benefits that accrue to users as a result of these features.

DESCRIPTION OF THE PREFERRED EMBODIMENT

Figure 1:
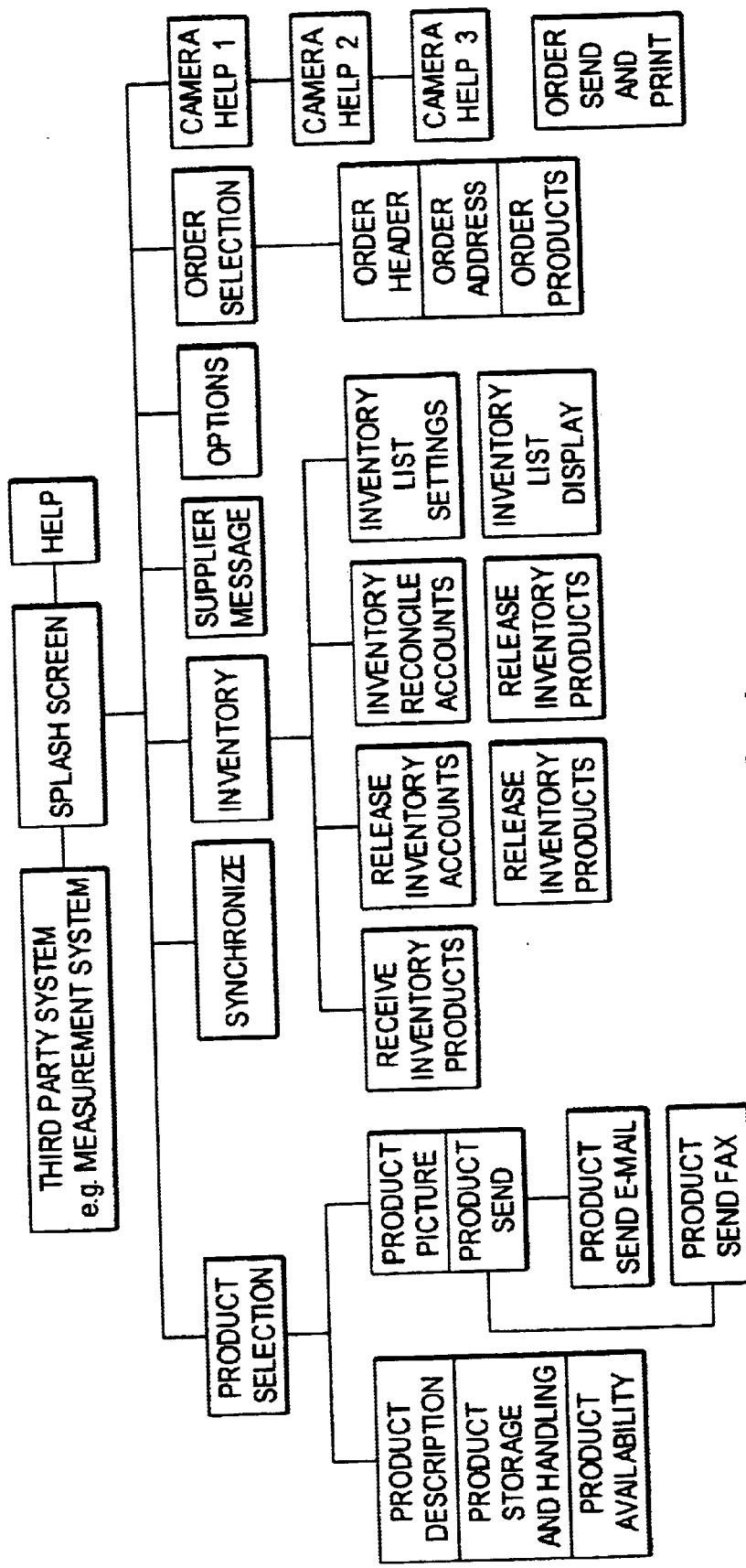
FIG. 1 illustrates a supplier's user interface hierarchy provided on a wireless mobile hand-held device.
Figure 2:
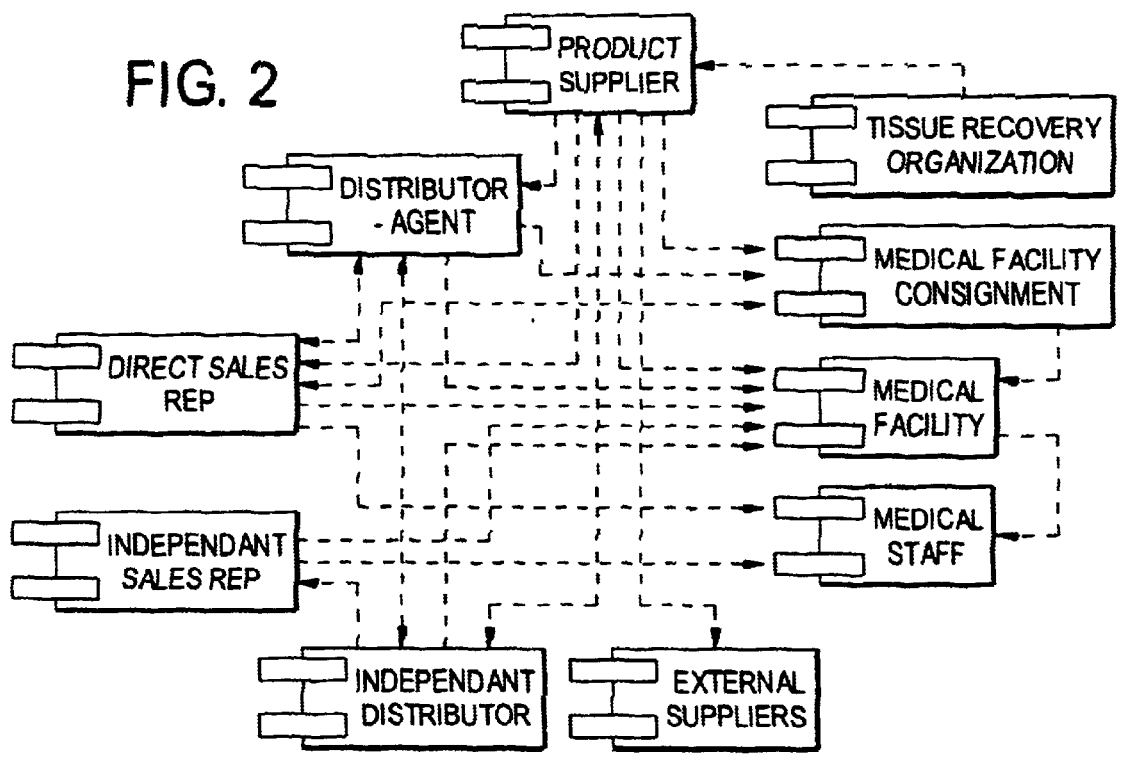
FIG. 2 illustrates normal inventory routes between components of a product Supply Chain and Medical Services Provider.

FIG. 1 illustrates a preferred embodiment of a supplier's user interface that may be provided on a wireless mobile hand-held device for use by a community of users including personnel of at least one Medical Services Provider and at least one Supply Chain of tissue and implant products. As used in the specification and claims, the term "tissue" is meant to include animal, including human, tissue, as well as synthetically manufactured materials, e.g., grafts. As illustrated in FIG. 2, a supplier of products is typically a chain of at least an independent Tissue Recovery Organization and an independent Product Supplier. External or third party suppliers as well as independent Sales Representatives and Distributors can also participate in a particular Supply Chain. Medical Services Providers comprise user organizations, such as hospitals including surgeons, clinics, or the like that interact with the Product Supply Chain components as illustrated in FIG. 2.

USER COMMUNITY

In a preferred embodiment, the wireless interface device is intended to be shared by multiple user types and therefore user administration capabilities are provided to manage access by authorized users. Various types of users are supported, comprising:

Primary supplier:
  i. Supplier employee,
  ii. Distributor-agent—interacts with sales representatives and supplier employees and transactions involve logistics of product inventory, and
  iii. sales representative—assists surgeons, doctors, and clinical staff in product selection and usage, interacts with other sales representatives and distributors resulting in multiple inventory transactions;

Tissue recovery organization—works independently of a medical facility to generate donor availability and harvest bone and tissue and is also responsible for completing governmental documentation and required reports;

Independents:
  Distributor—interacts with sales representatives and third party suppliers resulting in transactions involving the logistics of product inventory, and
  ii. Sales representative—interacts with medical staff, clinical staff, other sales representatives and distributors resulting in multiple inventory transactions;

Medical Services Provider:
  i. Consignment—the staff responsible for receiving and maintaining supplier-owned products that are physically stored at the Medical Services Provider's facilities and supplying this product when requested by others, resulting in multiple inventory transactions,
  ii. Facility—the clinical staff manages inventory at each independent medical facility monitoring product inventory levels, requesting replenishment of product as necessary directly from the sales representatives' on-hand inventory, a distributor, or directly from suppliers; while in the operating room the medical staff may request product directly from the medical facility's inventory and it is the responsibility of the clinical staff to fill the surgeon's request; clinical staff also comes into contact with patients and assigns product to patient records, and
  iii. Medical staff—never requests product directly from a supplier but employs the Measuring System, or a like subsystem, to provide detailed physical requirements and when in surgery requests product directly from the sales representatives' on-hand inventory or the consignment inventory of the medical facility resulting in multiple inventory transactions;

Third party or external supplier—interacts with all users resulting in multiple inventory transactions.

Inventory data is reported and tracked on multiple wireless mobile hand-held devices as users interact with one another, the possible interactions being illustrated in FIG. 2. For example, as described above, a Medical Facility may request product directly from a sales representative, on-hand inventory (consignment), a distributor-agent or directly from the supplier. However, in this embodiment, the medical staff never requests product directly from the supplier. Consignment inventory is owned by the supplier but resides in the facilities of and is managed by a Medical Services Provider.

SUPPLIER DATABASES

The supplier maintains several different databases on a base system, which is a Web-server, in a preferred embodiment.

1. product information database—is accessible by the wireless mobile hand-held device user and is administered so that access is restricted and the data is categorized and stored at least in one of the following registries: user, account, menu, product, order, inventory.

2. information database—is accessible by the wireless mobile hand-held device user and contains information that the supplier wishes to communicate to individuals who promote, distribute and track the supplier's products.

From the databases the operator can track any request for a user of the mobile hand held devices, such as inventory or ordering requests. The operator can, therefore, profile the user to and in use of the system, e.g., to anticipate the type and number of tissue/implants that a user may require in the future.

MOBILE DATABASES

Figure 3:
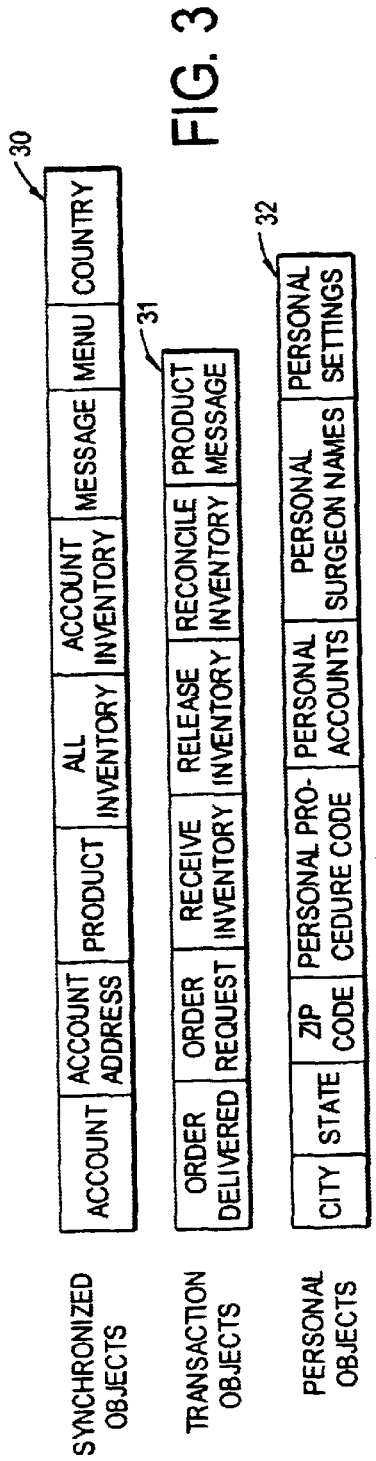
FIG. 3 illustrates objects of databases resident in the wireless mobile hand-held device.

Three types of objects, as illustrated in FIG. 3, can reside in the databases of each wireless mobile hand-held device:

synchronized objects 30—objects that are subject to being automatically synchronized to match the objects in the supplier's database;

transaction objects 31—objects that are designed to carry the content of a transaction from the databases of the wireless mobile hand-held device to the supplier's databases; and personal objects 32—objects that are maintained only by the user of the wireless mobile hand-held device.

MOBILE HAND-HELD SYSTEM

Figure 1A:
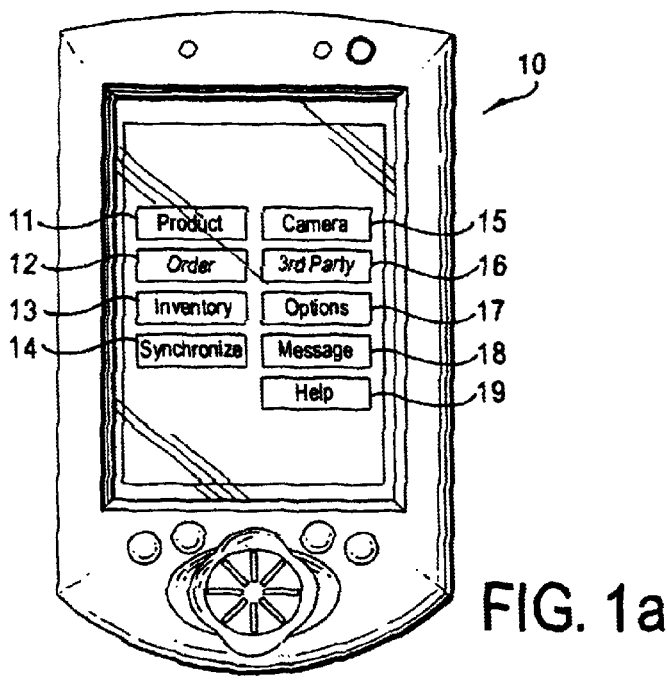
FIG. 1a illustrates a supplier menu of level 1 of the interface hierarchy illustrated in FIG. 1.

FIG. 1 illustrates a preferred embodiment of a system, according to the present invention, that is provided to a user of a wireless mobile hand-held device. A hierarchy of screens is illustrated in FIG. 1, with the first level 10 providing a menu of major functions available to the user, as illustrated in FIG. 1a:

Products 11—product selection menu organized by product type

Order 12

Inventory 13—inventory selection menu that comprises: List, Receive, Release, Reconcile and Read Bar Code Synchronize 14—synchronize pending information Camera 15

Measurement System 16—interface to an implementation of a measurement system, as described in U.S. Pat. No. 5,832,422, which allows precise measurements to be obtained from images such as x-rays, CT/MRI scans, or directly on Patient Options 17

Supplier Message 18—broadcasted messages from a supplier

Help 19

Both Bar Code (Inventory) and Camera functionality require a hardware device to be physically interfaced with the hand-held device and software to be installed to capture and process the inputs from these devices. These interfaces can be accomplished in a well known manner. Other functionality provided by the wireless mobile hand-held system comprises e-mail, facsimile, date selection, donor recovery, personal lists, as well as other functionally dedicated software or plug-compatible subsystems, e.g., an audio recorder or a modem.

By way of example only, in contrast to the hardware plugin approach of the device of U.S. Pat. No. 5,832,422, one such functionally dedicated subsystem employs the screen of the wireless mobile hand-held device to display an image of a target for tissue or implantation. The subsystem receives input from a user who indicates an area of the image data from this area of the target image is then subjected to processing, as selected by the user, to derive, e.g., adjusted measurements for product selection, customization, specification, and the like, and provide wireless/modem transmission of adjusted measurements.

SUPPLIER BASE SYSTEM

Figure 4:
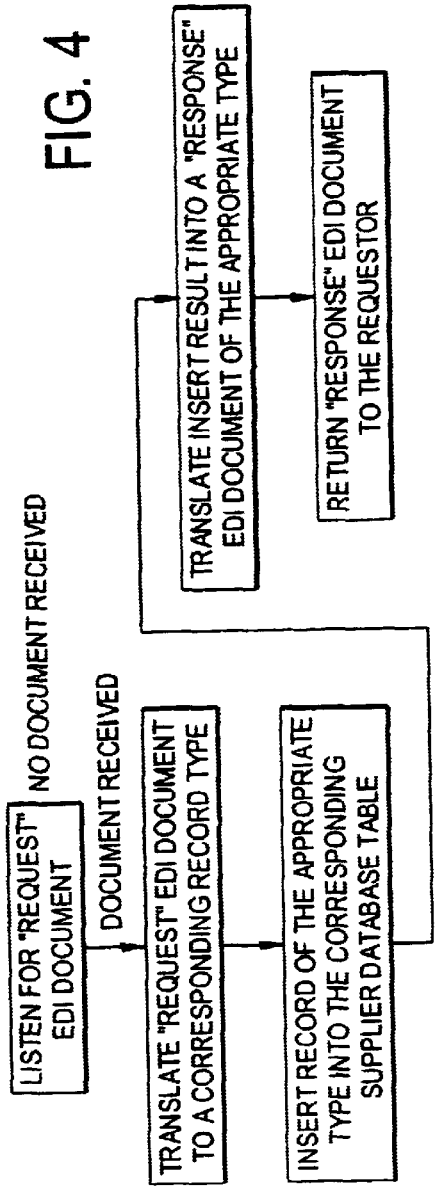
FIG. 4 is a flow sheet of a method of use.

In a preferred embodiment a supplier's base system is a Web-server that provides end user functionality and system administration services, comprising:

login/logout
backup mobile settings
restore mobile settings
synchronize products
synchronize accounts
synchronize menus
synchronize inventories
synchronize messages
new delivered order
new request order
receive inventory
release inventory
reconcile inventory
new e-mail message
new facsimile message
put menus
add user
remove user
update user
add product
remove product
update product
add account
remove account
update account
new message Each of these functions is activated, in a preferred embodiment, by a "request" Electronic Data Interchange (EDI) document from a requester using a wireless mobile hand-held device according to the present invention and employs a corresponding data table that is resident on a supplier's Web-server, to perform the request and return the "response" as an EDI document to the requester. A flow chart of this process is illustrated in FIG. 4.

Although we have described the use of the invention in connection with the obtaining, inventorying, ordering, supplying and tracking of tissue and implants, the system may be utilized in other environments, for example, to track pharmaceuticals through a distribution network, including manufacturer through patient use.

It will be appreciated by persons skilled in the art that the present invention is not limited to what has been particularly shown and described here in above. Rather, the scope of the present invention is defined only by the claims that follow.

APPENDIX I

| Supprting Features | Customer Benefits |
| --- | --- |
| PDA users are presented with supplier logo | Greater market visibility with display supplier logo |
| Supports global medical market place | Promotes global presense of supplier in all areas of medical product purchasing |
| Supports Measuring System: ie. 3$^{rd}$ party functionally | Ensures accurate sizing and variations of product |
| | Efficient use reduces waste of products due to incorrect product sizes |
| | Provision for calculation and storage of custom algorithms |
| Backup and restore users' settings | Quickly restores user to working status |
| | Handheld can easily be personalized for any user |
| Provides product description, techniques and uses, drawings and dimensions, codes and sizes, and pictures and videos | Provides the customer with accurate information needed to select the proper products to meet the patient needs |
| Ability to send high resolution literature and brochures via email, fax and print | A more efficient and powerful multi-media presentation to the customer prompts quicker response time |
| Processes automated email and fax transmissions | The efficient sharing of information saves the customer and sales representative valuable time |
| Provides a messaging marquee | Daily updates from the home office can be sent to all system users |
| | A rapid tool to send out a unified message to all users, or a select group of users |
| Provides print capability | Completes the custommer service cycle |
| | Customers receive a printed confirmation at point of delivery |
| Allows real time product availability, fee and product ordering information | Improved customer relations by providing instant access to online informtion |
| | Locating product for shipment is simplified through use of a detailed product location report |

APPENDIX I-continued

| Supprting Features | Customer Benefits |
|---|---|
| Provides an automated one-stop-shop: order, ship, bill, replenishment of product | Improved time management |
| Manage and track inventory with use of inquiries, lists and reconciliation tools | Promotes quicker response time between supplier and the client. Reduction in inventory handling related costs Provides tighter control of assets |
| Provides automated inventory controls | Increased and thorough invoicing of distributor products Quicker response time to supplier in reporting of inventory movements |
| Allows flexible data synchronization of supplier home office with handheld user | Ensures valid and timely information is shared and transmitted between home office and PDA user. |
| Provides helpful audit trails of product movement | Ensures accuracy of suppliers product distribution |
| Creates linkage of product to patient ID record | Improves the tracking of product implants A timesaving feature for the customer Product assignment is more likely to occur because of automated processing, which includes secure data transmission to supplier |
| Complies with HPPA and JCO | Full reporting of product and patient assignment through secure data transmissions |
| Provides wireless connectivity | Allows for transmission of data via a wireless and/or a modem to supplier |
| Implements fast and simple bar code scanning | Product misreprensentation is virtually eliminated Reduction of data entry error |
| Equipped with an attachable camera | Ability to store and send digital pictures and e-forms electronically to supplier |

I claim:

1. A method of inventorying a required implant or tissue product from a source of such products, the method comprising the steps of:

providing a wireless mobile hand held electronic device;

providing a data base for the inventory of implant or tissue products;

synchronizing the hand held electronic device with said data base to determine the inventory of implant or tissue products; and receiving an image selected from the group consisting of x-ray containing a measurement marker on the x-ray and a CT/MRI scan with a reference scale on the mobile hand held device.

2. The method of claim 1, including the step of using the measurement marker on the x-ray or scale on a CT/MRI scan to determine at least one of (1) a size of the implant, tissue product or any segment or (2) an angle on the image.

3. The method of claim 2, wherein the step of using the measurement is effected by employing software to enable the hand held electronic device to relate the measurement marker or reference scale, to the tissue product, implant or any object in the image.

4. A hand held electronic device for use in inventorying or ordering an implant or tissue product, said device comprising:

a display screen;

a wireless communication transceiver;

software to synchronize the hand held electronic device to a data base of an inventory of implant and tissue product products; and measuring means to determine the size and/or angle of an implant or tissue product from an x-ray or CT/MRI scan.

* * * * *